United States Patent [19]

Degenhardt et al.

[11] Patent Number: 4,877,603
[45] Date of Patent: Oct. 31, 1989

[54] ORAL COMPOSITIONS

[75] Inventors: Charles R. Degenhardt; Barbara A. Kozikowski, both of Cincinnati, Ohio

[73] Assignee: The Procter & Gamble Company, Cincinnati, Ohio

[21] Appl. No.: 276,995

[22] Filed: Nov. 28, 1988

Related U.S. Application Data

[63] Continuation-in-part of Ser. No. 135,164, Dec. 18, 1987, abandoned.

[51] Int. Cl.$^4$ .............................................. A61H 7/06
[52] U.S. Cl. ........................................ 424/57; 424/52
[58] Field of Search ...................................... 424/52, 57

[56] References Cited

U.S. PATENT DOCUMENTS

| | | | |
|---|---|---|---|
| 3,062,792 | 11/1962 | McConnell et al. | 260/85.5 |
| 3,297,578 | 1/1967 | Crutchfield et al. | 252/99 |
| 3,429,963 | 2/1969 | Stedlovsky | 424/56 |
| 3,535,421 | 10/1970 | Briner et al. | 424/52 |
| 3,544,509 | 12/1970 | Carroll et al. | 260/45.7 |
| 3,553,314 | 1/1971 | Francis | 424/49 |
| 3,553,315 | 1/1971 | Francis | 424/49 |
| 3,576,793 | 4/1971 | Carroll et al. | 260/80 |
| 3,621,081 | 11/1971 | Prentice | 260/924 |
| 3,678,154 | 7/1972 | Widder et al. | 424/52 |
| 3,737,522 | 6/1973 | Francis | 424/49 |
| 3,897,548 | 7/1975 | Katz | 424/54 |
| 3,934,002 | 1/1976 | Haefele | 424/54 |
| 3,959,458 | 5/1976 | Agricola et al. | 424/52 |
| 4,025,616 | 5/1977 | Haefele | 424/52 |
| 4,100,167 | 7/1978 | Selvarajan et al. | 260/296 R |
| 4,108,961 | 8/1978 | Ploger et al. | 424/57 |
| 4,108,962 | 8/1978 | Ploger et al. | 424/57 |
| 4,118,475 | 10/1978 | Gaffar et al. | 424/54 |
| 4,118,476 | 10/1978 | Gaffar et al. | 424/54 |
| 4,123,512 | 10/1978 | Gaffar | 424/54 |
| 4,137,303 | 1/1979 | Gaffar et al. | 424/52 |
| 4,138,477 | 2/1979 | Gaffar | 424/52 |
| 4,143,128 | 3/1979 | Kim et al. | 424/54 |
| 4,207,405 | 6/1980 | Masler, III et al. | 525/328 |
| 4,208,401 | 6/1980 | Bauman | 424/54 |
| 4,239,695 | 12/1980 | Chai et al. | 260/502.5 |
| 4,323,551 | 4/1982 | Parran, Jr. | 424/57 |
| 4,330,530 | 5/1982 | Baker | 424/131 |
| 4,342,857 | 8/1982 | Gaffar | 525/326.4 |
| 4,439,585 | 3/1984 | Gould et al. | 424/52 |
| 4,446,028 | 5/1984 | Becker | 252/180 |
| 4,446,052 | 5/1984 | Sunberg et al. | 424/54 |
| 4,661,341 | 4/1987 | Benedict et al. | 424/48 |
| 4,687,768 | 8/1987 | Benedict et al. | 514/102 |
| 4,772,461 | 9/1988 | Parran, Jr. et al. | 424/57 |

FOREIGN PATENT DOCUMENTS 1204967 9/1970 United Kingdom .
2089807 6/1982 United Kingdom .
2151478 7/1985 United Kingdom .

OTHER PUBLICATIONS

Anbar, M. and Farley, E. P., "Potential Use of Organic Pllyphosphonates as Adhesives in the Restoration of Teeth", *J. Dent. Res.*, Jul.–Aug. 1974, pp. 879–888.

Anbar, M. and St.John, G. A., "Adsorption of Polyphosphonated Polyethylene on Enamel of Teeth", *J. Dent. Res.*, May–Jun. 1971, vol. 50, No. 3, p. 778.

Anbar, M., St.John, G. A., and Scott, A. C., "Organic Polymeric Polyphosphonates as Potential Preventive Agents of Dental Caries: in vitro Experiments", *J. Dent. Res.*, Jul.–Aug. 1974, pp. 867–878.

Anbar, M., St.John, G. A., and Elward, T. E., "Organic Polymeric Polyphosphonate as Potential Preventive Agents of Dental Caries: in vivo Experiments", *J. Dent. Res.*, Sep.–Oct. 1974, pp. 1240–1244.

Francis, M. D., Martodam, R. R., "Chemical, Biochemical, and Medicinal Properties of the Diphosphonates", CRC Press, Inc., Boca Raton, Fla. (1983), Ch. 4, pp. 55–96.

Heins, A., Ploger, W., "Alkane-1,1-Diphosphonic Acids—Production, Properties and Technical Applications", from Lectures at Lolloquiums of the Bielefeld and Frankfurt Branches of Gesellschaft Deutscher Gehmiker 5/15-6/27/79.

W. W. Briner & M. D. Francis, "In Vitro and In Vivo Evaluation of Anti-Calculus Agents", Calculus Tiss. Res. 11, 10–22 (1973).

*Primary Examiner*—Paul Lieberman
*Assistant Examiner*—Willie J. Thompson
*Attorney, Agent, or Firm*—Leonard W. Lewis; Steven J. Goldstein; Jerry J. Yetter

[57] ABSTRACT

Anticalculus and antiplaque oral care compositions containing geminal diphosphonate polymer anticalculus agents and a pharmaceutically acceptable carrier, and method for inhibiting formation of calculus and plaque in the oral cavity by treatment with geminal diphosphonate polymers.

27 Claims, No Drawings

ORAL COMPOSITIONS

This is a continuation-in-part of application Ser. No. 135,164 filed on Dec. 18, 1987 now abandoned.

TECHNICAL FIELD

This invention relates to oral care compositions which contain anticalculus and antiplaque agents, and to a method for inhibiting the formation of calculus and plaque in the oral cavity.

BACKGROUND OF THE INVENTION

Dental calculus and plaque are two undesirable, but unfortunately common, dental conditions experienced by the general population.

Dental caculus, or tartar as it is sometimes called, is a deposit which forms on the surfaces of the teeth at the gingival margin. Supragingival calculus appears principally in the areas near the orifices of the salivary ducts; e.g., on the lingual surfaces of the lower anterior teeth and on the buccal surfaces of the upper first and second and on the distal surfaces of the posterior molars.

Mature calculus consists of an inorganic portion which is largely calcium phosphate arranged in a hydroxyapatite crystal lattice structure similar to bone, enamel and dentin. An organic portion is also present and consists of desquamated epithelial cells, leukocytes, salivary sediment, food debris and various types of microorganisms.

As the mature calculus develops, it becomes visibly white or yellowish in color unless stained or discolored by some extraneous agent. In addition to being unsightly and undesirable from an aesthetic standpoint, the mature caculus deposits are constant sources of irritation of the gingiva.

Another source of irritation in the oral cavity is plaque. Plaque is a combination of minerals and bacteria found in the mouth. The bacteria associated with plaque can secrete enzymes and endotoxins which can irritate the gums and cause an inflammatory ginigivitis. As the gums become increasingly irritated by this process, they have a tendency to bleed, lose their toughness and resiliency, and separate from the teeth, leaving periodontal pockets in which debris, secretions, more bacteria and toxins further accumulate. It is also possible for food to accumulate in these pockets, thereby providing nourishment for increased growth of bacteria and production of endotoxins and destructive enzymes.

Mechanical removal of calculus periodically by the dentist is, of course, routine dental office procedure. However, effective compositions and methods for inhibiting calculus formation between dental office visits are desirable for enhancing oral hygiene. A wide variety of chemical agents have been suggested in the art to retard calculus formation or to remove calculus after it is formed.

Inhibiting the formation of calculus between dentist visits has generally been accomplished with chemicals that involve chelation of calcium ion and/or crystal growth inhibition which prevents the calculus from forming and/or breaks down mature calculus by removing calcium.

The art discloses a number of chelating agents for this purpose. British Pat. No. 490,384, Feb. 15, 1937, discloses oral compositions containing ethylenediaminetetraacetic acid, nitrilotriacetic acid and related compounds as anticalculus agents. These anticalculus agents have relatively low effectiveness.

Also disclosed in the art are oral care compositions containing soluble pyrophosphate salts. Included among such disclosures are U.S. Pat. No. 2,941,926, June 21, 1960 to Salzmann et al. which discloses dental powders containing chlorophyll and pyrophosphate salts; U.S. Pat. No. 3,137,632, June 16, 1964 to Schiraldi, which discloses toothpastes containing pyrophosphate salts; U.S. Pat. No. 3,927,201 and 3,297,202, Dec. 16, 1975 to Baines et al. and Harvey et al., respectively, which disclose toothpastes which utilize soluble pyrophosphates as abrasives; U.S. Pat. No. 4,244,931, Jan. 13, 1981, and U.S. Pat. No. 4,247,526, Jan. 27, 1981 to Jarvis et al., which disclose pyrophosphate salts in dicalcium phosphate systems; Japanese Patent Application Disclosure No. 4945-1974, which discloses soluble pyrophosphates in a variety of dentifrice systems; U.S. Pat. No. 4,333,551, Apr. 6, 1982 to Parran, which discloses tetraalkali metal salts in mouthwash compositions; U.S. Pat. No. 4,515,772, May 7, 1985, to Parran et al., U.S. Pat. No. 4,590,066, May 20, 1986 to Parran et al., and U.S. Pat. No. 4,684,518, Aug. 4, 1987 to Parran et al., which disclose toothpaste compositions containing particular dialkali metal and tetraalkali metal pyrophosphate salts.

Mechanical removal of plaque and the minerals found which can collect near or underneath the gums which nourishes the bacteria which causes plaque is accomplished by conscientious oral care practitioners by brushing and flossing after meals. Mechanical removal, unfortunately, is not always completely thorough or effective, especially when not performed correctly and regularly. It is desirable to provide chemical compositions and methods which effectively inhibit plaque formation. These are preferably used in combination with mechanical methods of removal.

The art contains numerous disclosures of phosphonate materials useful as both anticalculus and antiplaque/antigingivitis agents in oral compositions. For example, U.S. Pat. No. 3,429,963, issued Feb. 25, 1969 to Shedlovsky, U.S. Pat. No. 4,102,993, issued July 25, 1978 to Gaffer, U.S. Pat. No. 4,042,679, issued Aug. 16, 1977 to Gaffer, U.S. Pat. No. 4,100,270, issued July 11, 1978 to Gaffer, U.S. Pat. No. 4,098,880, issued July 4, 1978 to Gaffer, U.S. Pat. No. 4,123,512, issued Oct. 31, 1978 to Gaffer, U.S. Pat. No. 4,138,477, issued Feb. 6, 1979 to Gaffer, and U.K. patent application No. 2,151,478, published July 24, 1985, Gaffer, all disclose polyvinyl phosphonate polymers having monophosphonate monomeric units. U.S. Pat. No. 3,553,315, issued Jan. 5, 1971 to Francis, discloses short chain carboxyphosphonic acid compounds. U.S. Pat. No. 3,553,314, issued Jan. 5, 1971 to Francis, U.S. Pat. No. 3,641,126, issued Feb. 8, 1972 to Prentice, and U.S. Pat. No. 3,737,522, issued June 5, 1973 to Francis, disclose nonpolymeric compounds having geminal diphosphonate groups.

U.S. Pat. No. 4,208,401, issued June 17, 1980 to Bauman, discloses a quaternary ammonium alkylene diphosphonate anticalculus agent having a geminal diphosphonate carbon. U.S. Pat. No. 3,678,154, issued July 18, 1972 to Widder et al., and U.S. Pat. No. 4,025,616, issued May 24, 1977 to Haefele, disclose polyphosphonate materials having one phosphonate group per carbon in the polymer backbone and phosphonate molecules having one geminal diphosphonate carbon atom.

While numerous materials as described above have been disclosed for use in oral compositions as anticalculus and antiplaque agents, there still exists a need for improved anticalculus and antiplaque agents.

It is an object of this invention to provide safe and effective anticalculus oral care compositions having good long term storage stability and high effectiveness.

It is a further object of this invention to provide oral care compositions, as described above, that provide both anticalculus activity and antiplaque activity.

It is another object of this invention to provide safe and effective anticalculus and antiplaque oral care compositions which, in addition to being stable and having high anticalculus and/or antiplaque effectiveness, can be made at commercially viable economic cost.

It is yet another object of this invention to provide a safe and effective method for inhibiting the formation of calculus and in the oral cavity. It is still another object of this invention to provide a safe and effective method for inhibiting the formation of both calculus and plaque in the oral cavity.

It is still a further object of this invention to provide a safe and effective method for inhibiting the formation of calculus and/or plaque which, in addition to providing anticalculus and antiplaque efficacy, can be implemented at commercially viable economic cost.

SUMMARY OF THE INVENTION

It has surprisingly been found that the objects of the present invention can be met by oral care compositions comprising geminal diphosphonate polymers and a pharmaceutically acceptable carrier. Specifically, such geminal diphosphonates include:

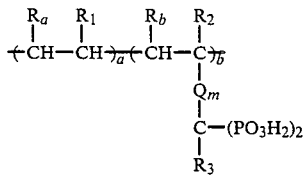

wherein each $R_1$, $R_2$, $R_a$, and $R_b$ can independently be H, $CO_2H$ or ester thereof, $-PO_3H_2$, $-C\equiv N$, substituted or unsubstituted aryl, substituted or unsubstituted $C_1-C_{10}$ alkyl, or substituted or unsubstituted $C_1-C_{20}$ oxyalkyl, each $R_3$ can independently be $-H$, $-OH$, amine, or substituted or unsubstituted $C_1-C_3$ alkyl, each m can independently be 0 or 1, each Q can independently be a substituted or unsubstituted aryl or a substituted or unsubstituted $C_1-C_{10}$ alkylene, and the ratio of a/b is greater than or equal to 0 and less than about 30;

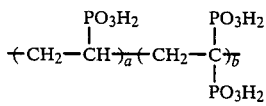

wherein a/b is greater than or equal to 0 and less than about 30; and (iii) polymerization products of

$$CH_2=CH-CH=C(PO_3X_2)_2$$

wherein each X can independently be $-H$ or a $C_1-C_{10}$ alkyl, and when X is an alkyl, each $-PO_3X_2$ group is converted to a $-PO_3H_2$ group subsequent to polymerization, and mixtures thereof;

said geminal diphosphate polymer having an average molecular weight of between about 1,000 and about 20,000 and an average of at least three geminal diphosphonate units per polymer chain.

DETAILED DESCRIPTION OF THE INVENTION

This invention pertains to geminal diphosphonate polymers, oral care compositions containing such geminal diphosphonate polymers specifically formulated for administration to the oral cavity without substantial ingestion, and methods for inhibiting calculus and plaque in the oral cavity. Applicable compositions include, but are not limited to, mouth washes, tooth pastes, powders, dentifrice compositions, topical solutions, prophylaxis pastes and gels, lozenges, gums, and the like.

Geminal Diphosphonate Polymers

Geminal diphosphonate polymers within the scope of the invention include the following three formulas:

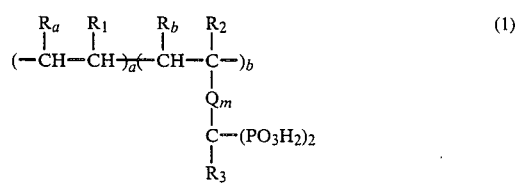

wherein: each $R_1$, $R_2$, $R_a$, and $R_b$ can independently be $-H$, $-CO_2H$ or ester thereof, $-PO_3H_2$, $-C\equiv H$, substituted or unsubstituted aryls, substituted or unsubstituted $C_1-C_{10}$ alkyls, or substituted or unsubstituted $C_1-C_{20}$ oxyalkyl, preferably $-H$, $-CO_2H$, $-PO_3H_2$, or unsubstituted $C_1-C_3$ alkyls, each $R_3$ can independently be $-H$, $-OH$, $C_1-C_3$ substituted or unsubstituted alkyl, or amine (including, but not limited to alkyl amines), preferably $-H$, $-OH$, or unsubstituted $C_1$ alkyl; each m can independently be 0 or 1, and each Q can independently be a substituted or unsubstituted aryl or a substituted or unsubstituted $C_1-C_{10}$ alkylene, preferably a $C_1-C_3$ alkylene; and the mole ratio of a/b is greater or equal to 0 and less than about 30, preferably less than about 20;

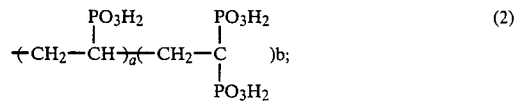

wherein
a/b is greater or equal to 0 and less than about 30, preferably less than about 20; and a geminal diphosphonate polymer formed from the polymerization of the monomer of Formula (3) as shown below:

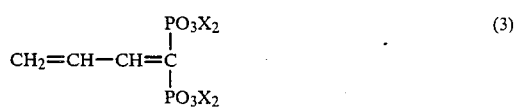

wherein each X can independently be $-H$ or a $C_1-C_{10}$ alkyl, preferably a $C_1-C_5$ alkyl, more preferably a $C_1-C_3$ alkyl, and most preferably a $C_2$ alkyl, and if X is not —H, each —PO$_3$X$_2$ group is converted to a —PO$_3$H$_2$ group subsequent to, or concurrent with, polymerization. This geminal diphosphonate polymerization of the Formula (3) monomer includes homopolymerization as well as copolymerization, terpolymerization, and the like, of said monomer along with other diphosphonate- or compatible nondiphosphonate-containing monomers. As used herein, "compatible nondiphosphonate-containing monomers" means monomers which do not significantly interfere with the anticalculus efficacy, and preferably the antiplaque efficacy, of the geminal diphosphonate groups.

As indicated by the above formulas, the geminal diphosphonate polymers of the present invention can have a geminal diphosphonate unit as part of the polymer backbone, as part of an alkyl or aryl group bonded to the polymer backbone, or as a mixture thereof. As used herein, the term "geminal diphosphonate" shall refer to chemical functionalities or monomeric units having a carbon atom with two phosphonate groups, or salts thereof, attached to that carbon atom.

As used herein, the term "polymer" with reference to the geminal diphosphate polymer of the present invention shall include polymers, copolymers, terpolymers, and the like. The term "polymer" shall also include oligomers so long as the molecular weight limitations of the present invention are met. The geminal diphosphonate polymers of the present invention shall include the phosphonic acid forms of the diphosphonate as well as pharmaceutically acceptable salts thereof, such as, but not limited to, alkali metal salts (e.g., sodium and potassium), alkali earth metal (e.g., calcium and magnesium), and ammonium or low molecular weight substituted ammonium (e.g., mono-, di-, and triethanol-ammonium) salts. At least about 3%, on a molar basis, of the monomeric units of the polymer should constitute or have substituted thereon a geminal carbon diphosphonate unit. Preferably at least about 5% of the monomeric units of the polymeric chain constitute, or have substituted thereon, a geminal diphosphonate unit. The non-geminal diphosphonate monomeric units should be geminal diphosphonate-compatible monomers. By "geminal diphosphonatecompatible monomers" is meant monomers which do not significantly interfere with the anticalculus, and preferably the antiplaque, efficacy of geminal diphosphonate groups.

As used herein, the symbols "a" and "b" shall refer to mole proportions and the ratio "a/b" shall therefore be a mole ratio. The ratio of a/b can be determined by using phosphorous-31 Nuclear Magnetic Resonance Spectroscopy (P$^{31}$NMR) techniques, said techniques being known to those skilled in the art.

The geminal diphosphate polymers of the present invention are also characterized by having molecular weights of at least about 1,000, preferably between about 1,000 and about 20,000, more preferably between about 1,000 and about 5,000, and most preferably between about 2,000 and about 5,000. As used herein, "molecular weight" shall refer to the weight average molecular weight as measured by the Low Angle Laser Light Scattering (LALLS) technique, said technique being known to those skilled in the art. It is undesirable for the molecular weight to be substantially lower than about 1,000 for safety concerns related to absorption into the bloodstream and effects upon bone remineralization and desorption. Anticalculus efficacy is believed to decrease as the ability of the geminal diphosphonate polymer to adsorb onto tooth or plaque material decreases. Molecular weights below about 20,000 are desirable since diphosphonate adsorption generally decreases with increasing molecular weight. Especially high anticalculus efficacy has been observed in the most preferred range between about 2,000 and about 5,000. The polymers of Formulas (1)-(3) are further characterized by having at least three geminal diphosphonate units per individual polymer chain.

Within the scope of geminal diphosphonate polymers of Formula (1) are the following preferred polymers:

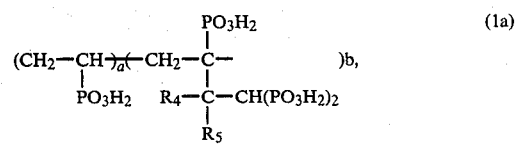

(1a)

wherein a/b is greater than or equal to 0 and less than about 30, preferably less than about 20 and, for practical considerations, generally greater than about 0.5, each R$_4$ can independently be H or a substituted or unsubstituted C$_1$-C$_{10}$ alkyl, preferably H or a C$_1$-C$_3$ unsubstituted alkyl, more preferably H, each R$_5$ can independently be H or a substituted or unsubstituted C$_1$-C$_{10}$ alkyl, preferably H or a C$_1$-C$_3$ unsubstituted alkyl, more preferably —H, and most preferably, both R$_4$ and R$_5$ are H;

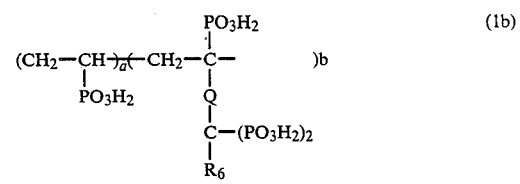

(1b)

wherein a/b is greater than or equal to 0 and less than about 30, preferably less than about 20 and for practical considerations, generally greater than about 0.5, each R$_6$ can independently be H, substituted or unsubstituted C$_1$-C$_{10}$ alkyl, preferably H or unsubstituted C$_1$-C$_3$ alkyl, more preferably H or CH$_3$, and each Q can independently be substituted or unsubstituted aryl, substituted or unsubstituted C$_1$-C$_{10}$ alkylene, preferably unsubstituted C$_1$-C$_3$ alkylene; and

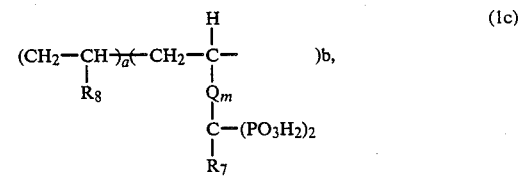

(1c)

wherein a/b is greater than or equal to 0 and less than about 30, preferably less than about 20 and for practical considerations, generally greater than about 0.5, m can be 0 or 1, preferably 0, Q can independently be substituted or unsubstituted aryl or a substituted or unsubstituted C$_1$-C$_{10}$ alkylene, preferably an unsubstituted C$_1$-C$_3$ alkylene, R$_7$ is OH or NH$_2$, preferably OH, or a salt thereof, and R$_8$ is CO$_2$H or C≡N, preferably CO$_2$H. The geminal diphosphonate polymers of Formula 1(c), wherein R$_7$ is —OH or a salt thereof and R$_8$ is —CO$_2$H, are especially preferred because it is believed that the hydroxylated geminal diphosphonate polymer is an especially effective oral calculus inhibitor, additionally it has antiplaque activity, and it can be made at significant economic savings relative to most other geminal diphosphonate polymers.

Synthesis of Geminal Diphosphonate Polymers

Diphosphonate polymers of the type described by Formula (1a) can be synthesized by dehydrogenation of polyvinylphosphonate followed by Michael addition of a geminal diphosphonate group, or addition of an ester therof followed by conversion to the acid form. Polyvinylphosphonate can be made from vinylphosphonate, which can be obtained commercially, for example, from Aldrich Chemical Co. (Milwaukee, Wis.), or can be made as described in the art (e.g., as described by Kosolapoff in J. Amer. Chem. Soc., Vol. 70, 1971–1972 (1948) and by Tavs and Weitkamp in Tetrahedron, Vol. 26, 5529–5534 (1970), both incorporated by reference herein.

The polymerization of unsaturated phosphonic acid and/or phosphonates is described by Sander and Steininger in J. Macromol. Sci. (Revs.), C1, 7–89 (1967), incorporated by reference herein. In general, the polymerization of vinylphosphonate can be carried out in accordance with the following description:

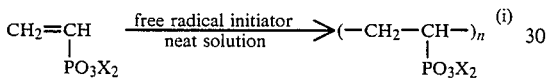

wherein the reaction is preferably carried out at about 60° C. to about 80° C. in neat solution with about 0.1 mole % to about 10 mole % (monomer basis) of a peroxide free radical such as benzoyl peroxide, hydrogen peroxide, and the like, and X is H or a $C_1$–$C_{10}$ alkyl, preferably a $C_1$–$C_5$ alkyl, and most preferably a $C_2$ alkyl; or

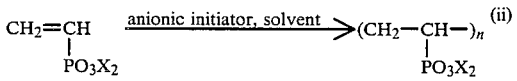

wherein X is as defined above, the anionic initiator can be a dialkyl amide, such as but not limited to lithium diisopropylamide, a metal halide, such as but not limited to potassium hydride, or preferably, an organometallic base such as n-butyl-lithium, napthalene-sodium, triethyl aluminum, and the like, and the reaction is carried out in a polar solvent such as THF, sulfolane, and the like, at low temperature, preferably below about −50° C., more preferably below about −70° C. Generally, between about 0.1 mole % to about 20 mole % of the anionic initiator is used (monomer basis). The molecular weight of the polymer formed from reaction (i) will generally be from about 1,000 to about 5,000. The molecular weight of the polymer formed from reaction (ii) can vary depending upon reaction conditions, but will generally be from about 5,000 toabout 20,000 at the preferred conditions. The geminal diphosphonate polymer can be formed by performing the following steps, which will also be readily understood by those skilled in the art:

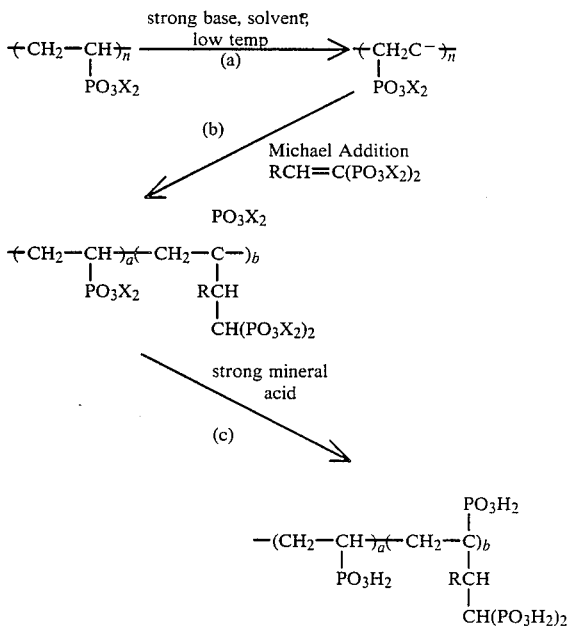

wherein, with respect to the Michael Addition reagent $RCH=C(PO_3X_2)_2$, X is a $C_1$–$C_{10}$ alkyl, preferably a $C_1$–$C_5$ alkyl, most preferably a $C_2$ alkyl, and each R can independently be H or a $C_1$–$C_{10}$, preferably a $C_1$–$C_3$ alkyl or H, most preferably H. The most preferred monomer, wherein X is $C_2$ alkyl (i.e., ethyl), is hereafter alternately referred to as $CH_2=C(PO_3Et_2)_2$, tetraethyl vinyldiphosphonate. The synthesis of preferred $RCH=C(PO_3X_2)_2$ monomers is described in further detail by Degenhardt and Burdsall in "Synthesis of Ethenylidenebis (Phosphonic Acid) and Its Tetraalkyl Esters," The Journal of Organic Chemistry, 1986, 51, 3488, incorporated by reference herein. Step (a) is performed using a strong base, preferably an organometallic base such as, but not limited to, n-butyllithium, naphthalene-sodium, and tetraethyl aluminum, or a dialkyl amide such as, but not limited to, lithium diisopropylamide, or a metal hydride such as, but not limited to, potassium hydride, and a polar solvent such as, but not limited to, THF and 1,2 dimethoxyethane, and the like at a temperature preferably below about −50° C., more preferably below about −70° C. The step (c) conversion to the phosphonic acid form can be performed by treatment with a strong minerl acid solution, such as HCl, $H_2SO_4$, $H_3PO_4$, and the like. The step (b) Michael Addition reaction can be performed by mixing the vinyl diphosphonate and the base-treated polymer in THF solution.

The diphosphonate polymers of Formula (1b) can be synthesized by the following reaction sequence which will readily be understood by those skilled in the art:

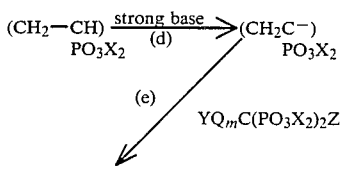

-continued

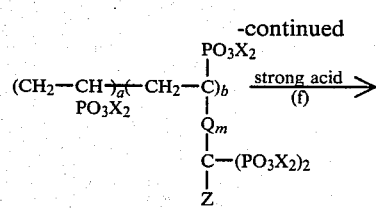

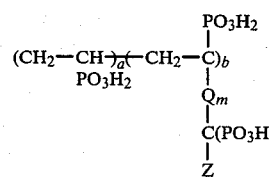

wherein steps (d) and (f) are performed as defined for steps (a) and (c) respectively, and Y is a halogen, preferably Cl, or sulfonate ester, Z is H or a $C_1$-$C_{10}$ alkyl group, preferably H or a $C_1$-$C_3$ alkyl group, most preferably H or $CH_3$, X is as defined above with reference to reaction (ii), m is either 0 or 1, and Q is a substituted or unsubstituted aryl or a substituted or unsubstituted $C_1$-$C_{10}$ alkylene, preferably a $C_1$-$C_3$ alkylene.

The preferred geminal diphosphonate polymers of Formula (1c) wherein $R_7$ is OH, or a salt thereof, can be synthesized by reacting phosphorous acid or a precursor of phosphorous acid which is capable of generating phosphorous acid in aqueous solution, such as $PCl_3$, in a polar organic solvent with a water-soluble carboxyl polymer. Preferred organic solvents are those in which the carboxyl polymer and the phosphorous acid or phosphorous acid precursor are essentially completely soluble so as to provide a homogeneous reaction mass. Typical preferred solvents are sulfolane (tetrahydrothiophene-1,1-dioxide), di-n-propyl sulfone, tetrahydrofuran (THF), 2-methyl THF, 3-methyl THF, tetrahydropyran and the like. The temperature of the reaction mass should be above its freezing temperature. The reaction is preferably carried out at a temperature in the range from about 0° C. to about 200° C., more preferably from about 50° C. to about 150° C.

The carboxyl polymer may be drived from an $\alpha$-$\beta$-olefinically unsaturated monomer having a carboxyl group. The carboxyl polymer can also be derived from an acid anhydride polymer derived from monomers readily converted to a carboxylic acid form. Preferred carboxyl polymers are those with at least 50% by weight with carboxylated or methyl-ester monomer units. Applicable polymers include polyacrylic acid, polymethacrylic acid, copolymers of acrylic acid and methacrylic acid, such as are commercially available; and polymaleic acid or polymaleic anhydride prepared as described by Normal G. Gaylor in J. Macromol. Sci. Revsi. Macromol. Chem., C13(2), 235–261 (1975); or copolymers of maleic anhydride with an olefin having from 2 to 4 carbon atoms; or a copolymer of maleic anhydride with a vinyl ether or vinyl ester or alkyl(meth)acrylate. The process for making such geminal diphosphonate polymers is described in further detail by Masler and Spaulding in U.S. Pat. No. 4,207,455, issued June 10, 1980, which is incorporated by reference herein.

Geminal diphosphonate polymer encompassed by Formula (1c) wherein $R_7$ is an amine and $R_8$ is $-C\equiv N$ can be made by reacting phosphorous acid or a precursor thereof with $(-CH_2-CH(RCN)-)_n$ as described byChai et al. in U.S. Pat. No. 4,239,695, issued Dec. 16, 1980, which is incorporated by reference herein, wherein, preferably, each $R^1$ independently is a $C_1$-$C_{10}$ aliphatic bridging radical.

Those skilled in the art will recognize that the processes disclosed above for synthesis of certain polymers described by Formula (1), each of said processes involving a step of attaching a geminal diphosphonate-containing group to a polymeric backbone, will ordinarily result in product having an a/b ratio greater than 0, for the reason that the reaction involving the geminal diphosphonate group, for example, the Michael addition during manufacture of a Formula (1a) type polymer, the displacement reaction during manufacture of a Formula (2b) type polymer, and the carboxyl polymer-phosphorous acid reaction product of Formula (1c), will generally not occur at all of the potential reaction sites on the polymer. If it is desired to have the ratio a/b by 0 or near zero, the pertinent reaction mentioned above can be designed to approach or, to the extent possible for the particular starting materials, achieve such goal, by, for example, increasing reagent concentration and/or reaction time, or by other methods which will be understood by those skilled in the art.

Another approach to achieve an a/b ratio of zero for the Formula (1) polymers is to homopolymerize a monomer having the following formula:

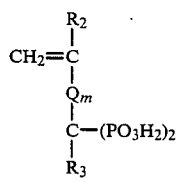

wherein $R_2$, $R_3$, m, and Q are as defined with respect to Formula (1). This homopolymerization is preferably carried out by anionic or free radical polymerization techniques. Free radical polymerization can be carried out utilizing free radicals such as benzoyl peroxide, hydrogen peroxide, and the like in neat solution or in a nonpolar solvent, preferably at about 60° C. to about 80° C. with about 0.1 mole % to about 10 mole % of the free radical, calculated on a monomer molar basis. Anionic polymerization is preferably initiated with an organometallic base such as n-butyllithium, naphthalenesodium, triethyl aluminum, and the like, and the reaction is carried out in a polar solvent such as THF, sulfolane, and the like, at low temperature, preferably below about −50° C., more preferably below about −70° C. Generally, between about 0.1 mole % to about 20 mole % of the anionic initiator is used (monomer basis).

Methods for synthesizing geminal diphosphonate polymers of the type described by Formula 2 wherein a/b is zero are known to those skilled in the art and have been disclosed, for example, by Carroll and Crutchfield in U.S. Pat. No. 3,544,509, issued Dec. 1, 1970, which is incorporated by reference herein. These diphosphonate polymers can be made by polymerization of lower alkylene-1,1-diphosphonate acids and metal salts thereof. Alternately, the diphosphonate polymers can be made from esters of lower alkylene-1,1-diphosphonate acids. Preferably the diphosphonate salts are converted to the free acid by treatment with a strong acid.

In addition to the diphosphonic acid and metal salt monomers of U.S. Pat. No. 3,544,509, monomers of the formula $RCH=C(PO_3X_2)_2$ as described above with reference to Formula (1a) synthesis can be used, and are in fact preferred.

Once polymerized, polymers formed from $RCH=C(PO_3X_2)_2$ can be converted to diphosphonic acid form by treatment with a strong mineral acid, such as $H_2SO_4$, HCl, $H_3PO_4$, and the like, as described by Worms and Schmidt-Dunker in "Organic Phosphorous Compounds," Volume 7, edited by Kosolapoff and Maier, pp 1-487 (1967), incorporated by reference herein.

Polymerization can be carried out by such methods as heating and/or using, as a catalyst, ultraviolet light, a free radical initiator, or an anionic initiator appropriate for use due to its solubility in the lower alkylene-1,1-diphosphonates and/or the medium used for polymerization, such as water and/or organic solvents. Free radical initiators include peroxides, including benzoyl peroxide, tolyl peroxide, hydrogen peroxide, and the like. Anionic initiators include organometallic reagents such as n-butyllithium, naphthalene-sodium, triethyl aluminum, and the like. The free radical or anionic initiators can be used in varying amounts. Generally from about 0.1% to about 5% by weight of the lower alkylene-1,1-diphosphonate is sufficient.

The diphosphonate polymers of Formula 2, wherein a/b is zero or greater than zero can be synthesized according to the following reaction sequence which will readily be understood by those skilled in the art:

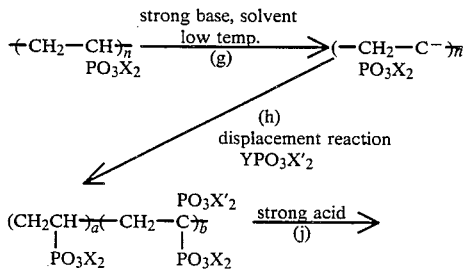

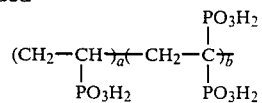

wherein steps (g) and (j) are performed as defined above for steps (a) and (c), respectively, Y is a halogen, preferably Cl, and X' is an aryl or $C_1$-$C_{10}$ alkyl, preferably an aryl or $C_1$-$C_5$ alkyl, more preferably an aryl or $C_2$ alkyl. The step (h) displacement reaction can be performed by adding the phosphoryl halide ($YPO_3X'_2$) to the THF solution of the base-treated polymer. In practice, the ratio of a/b will generally be greater than zero since all of the potential reaction sites on the polymer backbone will not experience the displacement reaction.

Geminal diphosphonate polymers formed from the monomers of Formula (3) can be prepared, in general, by 1,4 polymerization, 2,3 polymerization, or a combination thereof of the Formula (4) monomers.

Formula (3) monomer preparation and subsequent polymerization can be performed according to the exemplary method shown below.

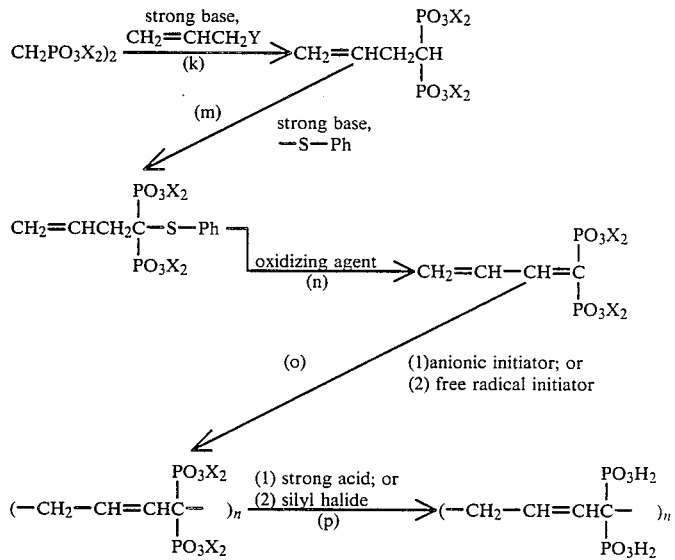

Referring to the methyl diphosphonate starting material, X can be H or a $C_1$-$C_{10}$ alkyl, preferably a $C_1$-$C_5$ alkyl, more preferably a $C_1$-$C_3$ alkyl, and most preferably a $C_2$ alkyl. Referring to reaction step (k), the strong base is preferably a metal hydride, such as, but not limited to, potassium hydride, and Y is a halogen, such as, but not limited to, bromine and chlorine. Referring to reaction step (m), the strong base can be the same as with respect to step (k), and —S—Ph represents a phenyl thiol leaving group which can be derived from compounds such as, but not limited to, diphenyl disulfide (PhSSPh) and S-phenylbenzenethiosulfonate ($PHSO_2SPh$). Referring to reaction step (n), such step can be carried out using conventional oxidizing agents. The polymerization reaction of reaction step (o) can be carried out with either anionic initiators, such as but not limited to organometallic bases, dialkyl amides, and metal hydrides as previously discussed herein or free radical initiators, such as but not limited to benzoyl peroxide and hydrogen peroxide, preferably free radical initiators. If X is not —H, conversion of the product of step (o) to the phosphonic acid form can be performed by treatment with a strong mineral acid or, preferably, with a silyl halide, such as but not limited to trialkyl silyl halides, e.g., trimethyl silyl bromide. Details of a preferred execution of this process can be found in Example IV.

Molecular weight can be varied by a variety of techniques which will be readily known to those skilled in the art. Without limiting the invention to any particular method, such molecular weight-varying techniques include choice of catalyst or free radical, choice of monomer, temperature, concentration, rate of stirring, etc. Molecular weight can also be manipulated by separation techniques, such as with a gel filtration column.

Oral Care Compositions

The oral care compositions include any composition containing a pharmaceutically safe and effective amount of one of the above geminal diphosphonate polymers for inhibiting the formation of calculus and pharmaceutically-acceptable carrier suitable for use in conjunction with oral administration. The compositions of the present invention are preferably formulated specifically for use in the oral cavity (ie. mouth) without being generally ingested, except as to any ingestion that may incidentally occur during usage. Thus, in the course of ordinary usage or treatment, the composition will be administered to the oral cavity and subsequently expunged after the usage or treatment. By "oral administration" and "administered to the oral cavity," or other analogous terms used herein is meant any activity by which the compositions of the present invention are administered into the mouth and contacted with the teeth and gums. As used herein, "oral administration" and "administration to the oral cavity" shall include contact with teeth and gums areas, as well as with any calculus or plaque that may already be formed in the oral cavity. Contact may occur by such nonlimiting activities as rinsing, brushing with a tooth brush, and directing a stream of water containing the composition toward the teeth and/or gum areas. The present invention embraces powders, pastes, gels, solutions, and the like, for rinsing, washing, or topical application in the oral cavity. These compositions include dentifrices, such as powders, pastes, gels, and liquids for cleaning teeth, prophylactic compositions, such as antigingivitis compositions and mouth rinses and other oral care compositions. Also included are compositions containing combinations of dentifrice, prophylactic, and other oral care ingredients.

By "pharmaceutically acceptable carrier", as used herein, is meant one or more diphosphonate-compatible solid or liquid diluents or encapsulating substances which are suitable for oral administration, but which needn't be suitable for ingestion of substantial quantities on a regular basis. By "diphosphonate-compatible", as used herein, is meant components of the composition that do not interact with the diphosphonate polymer, especially during storage, in a manner which would substantially reduce the composition's effectiveness for inhibiting formation of calculus and/or plaque. By suitable for "oral administration", as used herein, is meant suitable for application to or rinsing of the interior, or cavity, of ones mouth, or a part thereof.

The concentration of geminal diphosphonate polymer in the oral care composition is at least an effective amount for providing anticalculus efficacy (i.e., calculus-inhibiting utility). Preferably the concentration of geminal diphosphonate polymer in the oral composition will be between about 0.1% and about 20%, by weight. Generally the oral care composition will contain between about 1% and 10%, most generally between 1% and about 5%.

By "safe and effective amount" as used herein is meant an amount of a geminal diphosphonate polymer high enough to provide anticalculus and/or antiplaque efficacy, preferably both, but not so high as to fall outside the scope of sound medical judgment. The safe and effective amount of the geminal diphosphonate polymer can vary with the particular polymer chosen, the duration of treatment, and the particular carrier from which the geminal diphosphonate polymer is applied and other considerations as may be apparent to one skilled in the art. Generally an amount of at least about 0.025 grams of the geminal diphosphonate polymer administered on a regular basis, e.g., one or more times per day, to the oral cavity in such oral care products as described above under the conditions and circumstances in which such products are conventionally utilized effective for inhibiting formation of calculus. Optionally, at least about 0.050 grams is administered in a regular basis. These same amounts can also be effective for inhibiting the formation of plaque in the oral cavity. Generally, the amount of geminal diphosphonate polymer administered orally is less than about 5 grams per oral administration.

The oral care compositions of the present invention preferably have a pH of between about pH 5.0 and about pH 11.0. A preferred pH range is from about pH 7.0 to about pH 10.0. The pH of the composition, of course, is determinative of the predominant salt form of the diphosphonate polymers present therein. Preferably the composition is buffered, for example, by including a buffer in the carrier, such that a pH of between about pH 5.0 and about pH 11.0, more preferably between about pH 7.0 and about pH 10, is maintained in the oral cavity during use. Exemplary nonlimiting buffers include citrate, citrate/bicarbonate, and phosphate buffers.

The carrier can additionally comprise the usual and optional components of the particular type of oral composition desired. Such additional components can include abrasives, sudsing agents, flavoring agents, sweetening agents, antiplaque agents, antitartar agents, antigingivitis agents, coloring agents, pigments, humectants, binders (thickening agents), fluoride anticaries agents, etc. The choice of carrier to be used is basically determined by the way the composition is to be introduced to the oral cavity and by the purposes, in addition to inhibiting formation of calculus, for which the composition is meant to be effective. For example, if a toothpaste is to be used, then a "toothpaste carrier" is chosen as disclosed in, e.g., U.S. Pat. No. 3,988,433, to Benedict, the disclosure of which is incorporated herein by reference (e.g., abrasive materials, sudsing agents, binders, humectants, flavoring and sweetening agents, etc.), or if a mouth rinse is to be used, then a "mouth rinse carrier" is chosen, also as disclosed in, e.g., U.S. Pat. No. 3,988,433 to Benedict (e.g., water, flavoring and sweetening agents, possibly an organic solvent such as ethanol, etc.). Similarly, if a mouth spray is to be used, then a "mouth spray carrier" which can be similar to mouth rinse carriers as described above, is chosen and, depending upon the type of application chosen, a propellant may also be included; if a chewing gum is to be used, then a "chewing gum carrier" is chosen, as disclosed in, e.g., U.S. Pat. No. 4,472,373, to Ryan, and in U.S. Pat. No. 4,083,955, to Grabenstetter et al., both of which being incorporated herein by reference (e.g., gum base, flavoring and sweetening agents); and if a sachet is to be used, then a "sachet carrier" is chosen (e.g., sachet bag, flavoring and sweetening agents). Carriers suitable for the preparation of compositions of the present invention are well known in the art. Their selection will also depend on secondary considerations like taste, cost, shelf stability, which are not critical for the purpose of the present invention, and can be made without difficulty by a person skilled in the art.

The abrasive polishing material contemplated for use in the present invention can be any material which does not excessively abrade dentin. These include, for example, silicas including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and others such as disclosed in U.S. Pat. No. 3,070,510, Cooley et al., Dec. 25, 1962, incorporated herein by reference. Mixtures of abrasives may also be used. Preferably, the abrasives used are not large sources of soluble calcium such that the crystal growth inhibiting capacity of the diphosphonate polymer is significantly depleted. For this reason, conventional abrasives such as calcium carbonate and dicalcium orthophosphate are preferably not used, or are present in small quantities relative to the diphosphonate polymer such that significant anticalculus efficacy is maintained, or are not contacted with the diphosphonate polymer until shortly before or simultaneously with delivery to the oral cavity. However, predominantly -phase calcium pyrophosphate such as that prepared in accordance with Schweizer, U.S. Pat. No. 3,112,247, issued Nov. 26, 1963, which contains relatively little soluble calcium, can be used and is a preferred abrasive. Other preferred abrasives include alumina insoluble metaphosphate, and the resinous abrasives of U.S. Pat. No. 3,070,510.

Silica dental abrasives, of various types, can provide exceptional dental cleaning and polishing performance without unduly abrading tooth enamel of dentin. Silica abrasive materials are also believed to be exceptionally compatible with phosphate materials as well as with sources of soluble fluoride. For these reasons they are especially preferred for use herein.

The silica abrasive polishing materials useful herein, as well as the other abrasives, generally have an average particle size ranging between about 0.1 and about 30 microns, preferably between about 5 and about 15 microns. The silica abrasive can be precipitated silica or silica gels such as the silica xerogels described in Pader et al., U.S. Pat. No. 3,538,230, issued Mar. 2, 1970 and DiGiulio, U.S. Pat. No. 3,862,307, June 21, 1975 both incorporated herein by reference. Preferred are the silica xerogels marketed under the tradename "Syloid" by the W. R. Grace & Company, Davison Chemical Division. Preferred precipitated silica material include those marketed by the J. M. Huber Corporation under the tradename "Zeodent." These silica abrasives are described in U.S. Pat. No. 4,340,583, July 29, 1982, incorporated herein by reference.

The abrasive in the compositions described herein is preferably present at a level of from about 6% to about 70%, more preferably from about 15% to about 25% when the dentifrice is a toothpaste. Higher levels, as high as 90%, may be used if the composition is a tooth powder.

An ingredient preferably incorporated into dentifrice compositions such as toothpastes is a sudsing agent. Suitable sudsing agents are those which are reasonably stable and form suds throughout a wide pH range, i.e., non-soap anionic, nonionic, cationic, zwitterionic and amphoteric organic synthetic detergents. Sudsing agents of these types are described more fully in Agricola et al, U.S. Pat. No. 3,959,458, issued May 25, 1976, and in Haefele, U.S. Pat. No. 3,937,807, issued Feb. 10, 1976, both of these patents being incorporated herein by reference.

Anionic sudsing agents useful herein include the watersoluble salts of alkyl sulfates having from 10 to 18 carbon atoms in the alkyl radical and the water-soluble salts of sulfonated monoglycerides of fatty acids having from 10 to 18 carbon atoms. Sodium lauryl sulfate and sodium coconut monoglyceride sulfonates are examples of anionic surfactants of this type. Mixtures of anionic surfactants can also be employed.

The nonionic sudsing agents which can be used in the compositions of the present invention can be broadly defined as compounds produced by the condensation of alkylene oxide groups (hydrophilic in nature) with an organic hydrophobic compound which may be aliphatic or alkylaromatic in nature. Examples of suitable nonionic sudsing agents include the Pluronics TM (Wyandotte Chemicals Corp., Wyandotte, Mich.), polyethylene oxide condensates of ethylene oxide with the reaction product of propylene oxide and ethylene diamine, ethylene oxide condensates of aliphatic alcohols, long chain tertiary amine oxide, long chain tertiary phosphine oxides, long chain dialkyl sulfoxides and mixtures of such materials.

The zwitterionic synthetic sudsing agents useful in the compositions of the present invention can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, orphosphonate.

The cationic sudsing agents useful in the compositions of the present invention can be broadly defined as quaternary ammonium compounds having one long alkyl chain containing from about 8 to about 18 carbon atoms such as lauryl trimethylammonium chloride; cetyl pyridinium chloride, cetyl trimethylammonium bromide, di-isotubylphenoxyethoxyethyl-dimethylbenzylammonium chloride; coconutalkyltrimethylammonium nitrite; cetyl pyridinium fluoride; etc.

The amphoteric sudsing agents useful in the present invention can be broadly described as derivatives of aliphatic secondary and tertiary amines in which the aliphatic radical can be straight chain or branched and wherein one of the aliphatic substituents contains from about 8 to about 18 carbon atoms and one contains an anionic water-solubilizing group, e.g., carboxylate, sulfonate, sulfate, phosphate, or phosphonate.

The sudsing agent can be present in the compositions of this invention in an amount from about 0% to about 10% by weight of the total composition.

Flavoring agents can also be added to the instant compositions. Suitable flavoring agents include oil of wintergreen, oil of peppermint, oil of spearmint, oil of sassafras, and oil of clove. Sweetening agents which can be used include saccharin, dextrose, levulose, aspartame, D-tryptophan, dihydrochalcones, acesulfame and sodium cyclamate. Flavoring agents are generally used in the composition at levels of from about 0.4% to about 2% by weight and sweetening agents at levels of from about 0.1% to about 5% by weight.

Binders can also be used with the toothpastes of the present inventions. Such binders include, for example, xanthan gum, carrageenan, Irish moss, Viscarin ®, and carboxyvinyl polymers. These binders are generally present at a level of from about 0.1% to 1%.

Other antiplaque agents can also optionally be added to the compositions of this invention. Suitable antiplaque agents may include bis-biguanide compounds such as chlorhexidine (1,6-bis [$N^5$-pchlorophenyl-$N^1$-biguanido]hexane), the soluble and insoluble salts thereof, and related materials such as 1,2-bis($N^5$-p-trifluoromethylphenyl-$N^1$-biguanido)ethane. These compounds are described more fully in Haefele, U.S. Pat. No. 3,923,002, issued Jan. 20, 1976; Haefele, U.S. Pat. No. 3,937,807, issued Feb. 10, 1976; Procter & Gamble, Belgian Pat. No. 843,244, published Dec. 22, 1976 and Procter & Gamble, Belgian Pat. No. 844,764, published Jan. 31, 1977. These patents are incorporated herein by reference. The composition of the present invention can also contain other anticalculus agents, or antitartar agents, such as the dialkali metal and mixtures of dialkali metal and tetraalkali metal pyrophosphate salts described by Parran, Jr. et al. in U.S. Pat. Nos. 4,515,772, 4,590,006, and 4,684,518, respectively issued Mar. 19, 1984, Feb. 19, 1985, and Aug. 4, 1987. If present, the optional antiplaque agents generally comprise from about 0% to about 5% by weight of the compositions herein.

Another optional component of the compositions herein is a humectant. The humectant serves to keep the compositions such as toothpaste from hardening upon exposure to air and in mouthwashes give a moist feel to the mouth. Certain humectants can also impart desirable sweetness of flavor to mouthwash and toothpaste compositions. The humectant, on a pure humectant basis, generally comprises from 0% to 70%, preferably from 0% to 55%, by weight of the compositions herein.

Suitable humectants for use in this invention include edible polyhydric alcohols such as glycerine, sorbitol, xylitol and propylene glycol. Sorbitol is frequently employed as a 70% aqueous solution. The humectant ranges in the above paragraph, however, are based upon the pure sorbitol component of such solutions.

The topical solutions and mouth rinses herein may also contain ethanol in an amount preferably of from about 0% to about 30%.

Suitable coloring agents include any pharmaceutically acceptable food or drug coloring acceptable for topical application in the oral cavity.

Water can also be present in the compositions of this invention. Water employed in the preparation of commercially suitable dentifrices, prophylactic compositions, and other oral care compositions should preferably be deionized and free of organic impurities. Water generally comprises from about 10% to 50%, preferably from about 20% to 40%, by weight of the toothpaste compositions herein. Mouth rinses generally contain from about 45% to about 95% water. These amounts of water include the free water which is added plus that which is introduced with other materials such as with sorbitol.

It is common to have a water-soluble fluoride compound present in dentifrices in an amount sufficient to give a fluoride concentration of from about 0.0025% to about 5.0% by weight, preferably from about 0.005% to about 2.0% by weight, to provide additional anticaries efficacy. Preferred fluorides are sodium fluoride, stannous fluoride, indium fluoride, and sodium monofluorophosphate. Norris et al., U.S. Pat. No. 2,946,735, issued July 26, 1960, and Widder et al., U.S. Pat. No. 3,678,154, issued July 18, 1972, disclose such salts, as well as others, and are incorporated by reference herein.

Rat Calculus Test

The following test method is useful for obtaining in vivo data on the calculus inhibition properties of geminal diphosphonate polymers of the present invention, and for comparing their performance with other phosphonate anticalculus agents.

Two or more groups of 22 to 23-day old Wistar strain rats, each group comprising one member of each of 30 litters, are employed in this test, one group serving as the control and the other serving as the test group. Each group is balanced for weight and sex. The control group of animals is placed on a calculus inducing diet consisting of 50% cornstarch, 32% non-fat dry milk, 5% celluflour, 5% powdered sucrose, 3% liver powder, 2.7% $NaH_2PO_4.H_2O$, 1% vegetable oil, 1% $CaCl_2.H_2O$, and 0.3% $MgSO_4$. The animals are fed ad libitum. The animals are provided with deionized water only for fluid replenishment. Each animal in the test group(s) is administered an anticalculus agent twice daily, five days per week by contacting their teeth with an anticalculus agent-soaked cotton-tipped applicator.

Three weeks after the commencement of the test, the animals are sacrificed and their molars are graded for severity of calculus by assessing the area and depth of accumulation on each of 44 orally exposed tooth surfaces examined in each animal. Grading is made on a 0–3 scale for each surface, 0 being no detectable calcified deposits, 0.5 being moderate to heavy accumulation on 10% or less of the tooth surface area or light accumulation on 25% or less of the area, 1 being moderate to heavy accumulation on 10% to 25% of the area, 2 being light to moderate accumulation of 25% to 50% of the area or heavy accumulation on 25% to 50% of the area, and 3 being moderate accumulation on greater than 75% of the area or heavy accumulation on 50% or more of the area. The total calculus score for each animal is determined by adding the grades for each of the 44 surfaces.

Crystal Growth Inhibition Determination

The following test method is useful for obtaining in vitro calculus inhibition data on the geminal diphosphonate polymers compositions of the present invention, and for comparing those results with the performance of other phosphonate anticalculus agents.

As hereinbefore stated, the geminal diphosphonate polymers inhibit the growth of calcium hydroxylapatite crystals and in this way interfere with the normal formation of calcium hydroxylapatite from solution. This test determines the effects of the geminal diphosphonate polymers on the calcium phosphonate formed on addition of calcium ion to orthophosphate ion at constant pH. The test is described in detail by Nancollas, et al., Oral Biol. 15, 731 (1970), the disclosure of which is incorporated herein by reference.

In this test, hydroxyapatite seed crystals are added to a calcium/phosphate solution supersaturated with respect to induced precipitation of calcium phosphates but meta-stable toward spontaneous precipitation. The seed crystals induce precipitation and crystal growth. Test chemicals are added to the meta-stable Ca/P solution before seeding. The effect of these chemicals on formation of hydroxyapatite induced by seed crystals has been shown to correlate with in vivo effects of these chemicals on calcium metabolism.

Formation of calcium phosphate crystals results in the release of hydrogen ions (i.e., pH change). The rate of crystal growth is monitored by observing the addition of base required to maintain a constant pH. Low levels ($1 \times 10^{-6}$M) geminal polydiphosphonates are capable of inhibiting the formation of calcium phosphate for 20 minutes or longer. Crystal growth inhibition depends on the propensity of the polyphosphonates or geminal polydiphosphonates to adsorb on calcium phosphate crystal nuclei.

Anti-Adherance Test

The following test method is useful for obtaining in vitro antiplaque data on the geminal diphosphonate polymers of the present invention. The test measures bacterial adherence on hydroxyapatite beads.

25 mgs. of hydroxyapatite (HAP) beads are precoated with human saliva for 1.5 hours. The HAP beads are then washed three times with a buffer solution of 0.05M KCl, 1 mM $PO_4$ (pH 6.0), 1 mM $CaCl_2$ and 0.1 mM $MgCl_2$. The HAP beads are then equilibrated with an aqueous solution of a geminal diphosphonate polymer (at a desired concentration such as 5%), at pH 7.0, for 5 minutes with agitation. The HAP beads are removed from the aqueous solution and then washed once with a buffer solution as described above.

For the adsorption studies bacteria 25 mg of the HAP beads prepared as described above are placed in 1.0 ml of a cell suspension comprising about $1.5 \times 10^8$ bacteria (S. sanguis) in a buffer solution as described above. The beads are equilibrated in the mixture of three hours, with agitation. The beads are allowed to settle for one minute and the supernatant, which contains unadsorbed cells, is removed. The HAP beads are washed three times with buffer solution (same composition as described above), collected by filtration, and dissolved in hydrochloric acid. Radioactivity of the dissolved HAP is then measured by liquid scintillation counts in order to determine the number of bound cells. These results are compared to the radioactivity of dissolved HAP that was prepared as a control without anticalculus/antiplaque agents.

The following examples are included to illustrate the present invention; it is not intended to limit the scope of the invention to the exemplified subject matter. The scope of the invention is defined by the claims which follow these examples.

EXAMPLE I

The example shows the synthesis of a polyvinyldiphosphonate polymer of the type described by Formula (1b). The following steps were performed:

(a) Tetraethyl vinyldiphosphonate synthesis:

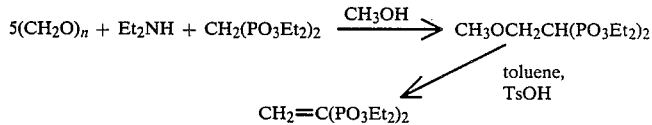

Specifically, 104.2 grams (3.47 moles) of paraformaldehyde and 50.8 grams (0.69 moles) of diethylamine were combined in 2.0 liters of dry methanol and the mixtuure was heated until clear. (As used above and hereafter, "Et" shall refer to an ethyl group.) The heat was removed and 200.0 grams (0.69 moles ) of tetraethyl methylenebisphosphonate was added. The mixture was refluxed for 24 hours, then an additional 2.0 liters of methanol were added and the solution was concentrated under vacuum at 30° C. Five hundred (500) milliliters of toluene was added and the solution was again concentrated under vacuum at 30° C. to ensure complete removal of methanol from the intermediate product which intermediate product is a clear liquid. Next, 1.0 liter of toluene and 50.0 milligrams p-toluenesulfonic acid monohydrate were added to the intermediate product and the solution was refluxed overnight in a 2.0 liter flask equipped with a Soxhlet extractor having 4 Angstrom molecular sieves. Methanol was removed by adsorption into these molecular sieves. The solvent (toluene) was removed under vacuum after 14 hours of reflux to provide the crude product. The crude product was dissolved in 1.0 liter chloroform and twice washed with 150 milliliters of distilled water. The chloroform solution was dried over anhydrous $MgSO_4$ concentrated, and then distilled to product 134.2 grams of the desired product, tetraethyl vinyldiphosphonate. The boiling point at 0.07 mm Hg was 121° C.

(b) Polyvinyldiphosphonate polymer synthesis:

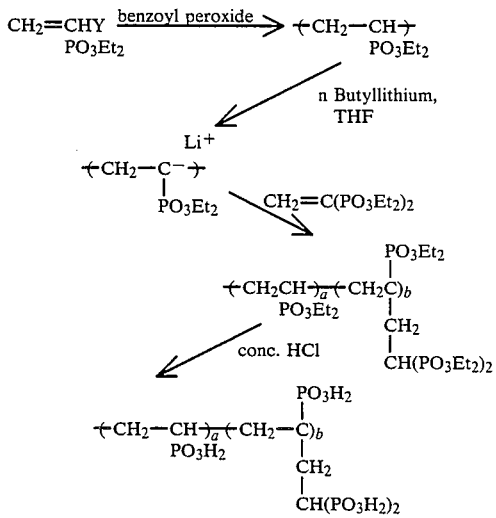

To begin the diphosphonate polymer synthesis, 96.8 grams (0.59 moles) of polydiethylvinylphosphonate and 2.0 liters tetrahydrofuran (THF), freshly distilled from LiAlH4, were added to a 5.0 liter, three-neck, round-bottom flash equipped with a mechanical stirrer, a 500 milliliter addition funnel, and an inlet. The solution was stirred at room temperature until the polymer was essentially completely dissolved. The solution was then chilled to −78° C. and stirred for one hour with 192.9 milliliters of 1.55N (in hexane) of n-butyllithium (0.30 moles). Next, 89.7 grams of $CH_2=C(PO_3Et_2)_2$ (0.30 moles) were added and the temperature of the solution was maintained at −78° C. for one hour with stirring. The solution was then allowed to warn to room temperature with stirring. Seventy-five (75) milliliters of distilled water were added and the solution was concentrated to provide a residue. The residue was dissolved in 1500 milliliters concentrated HCl (12 molar), refluxed for four hours, and reconcentrated to provide crude polyvinyldiphosphonate polymer product. The crude product was chromatographed on Sephadex™ G-25 resin (available from Pharmacia Inc., Piscataway) having a 5,000 molecular weight cutoff to provide 41 grams of a purified product having an average molecular weight of about 9500, as determined by low angle laser light scattering (LALLS). The ratio of a/b, as determined by $p^{31}$NMR analysis, was about 2.5.

EXAMPLE II

This example shows the synthesis of a geminal polydiphosphonate polymer of the type described by Formula (2) wherein the ratio of a/b is greater than zero. The following steps were performed:

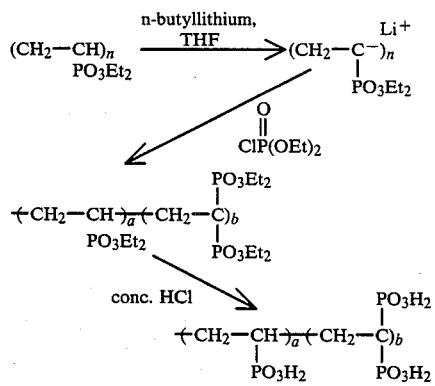

Specifically, 114.42 grams of polyvinyldiethylphosphonate (0.70 moles) and 1.9 liters THF (freshly distilled from LiAlH4) were mixed in a 5 liter, 3-neck, round-bottom flask equipped with a mechanical stirrer, a 500 milliliter addition funnel, and Ar inlet at room temperature until the polymer was essentially completely dissolved. After chilling the solution to −78° C., 225 milliliters of 1.55N (in hexane) n-butyllithium (0.35 moles) were added dropwise and the solution was mixed for one hour at −78° C. Next, 60.1 grams of diethyl chlorophosphate (0.35 moles) were added and the solution was allowed to warm to room temperature with stirring. The solution was then cooled to −78° C., treated with n-butyllithium and diethyl chlorophosphate, and warmed to room temperature as described above. Fifty (50) milliliters of distilled water were added and the solution was concentrated to provide a residue of the product. The residue was refluxed with 750 milliliters concentrated HCl (12 molar) for three hours and reconcentrated to provide the crude product. The crude product was chromatographed on Sephadex™ G-25 resin (5000 molecular weight cutoff), available from Pharmacia Inc., to provide 33.1 grams of the desired diphosphonate polymer. The ratio of a/b, as determined by $P^{31}$NMR analysis was about 2.6.

EXAMPLE III

This example shows the synthesis of a preferred geminal diphosphonate polymer of the type described by Formula (1c).

Specifically, 125.0 grams of polyacrylic acid (1.44 moles, average molecular weight of 2100 as determined by LALLS), 25.9 grams of distilled water (1.44 moles), and 300.0 grams of sulfolane (tetramethylene sulfone) were mixed in a two (2) liter, round-bottom flask. This solution was stirred at 45° C. until the polyacrylic acid was dissolved. Next, 125.6 milliliters of PCl3 (197.76 grams, 1.44 moles) were dripped into the solution with continual stirring over a period of approximately one (1) hour. Liberated HCl was removed from the flask with an argon purge. The solution was heated to 100° C. by placing the flask in an oil bath and maintained at that temperature for two (2) hours before allowing the solution to cool to room temperature. Once at room temperature, 600 milliliters of CHCl3 were poured into the flask which caused a yellow solid precipitate to fall out of solution. The precipitate was collected by vacuum filtration and washed with CHCl3 five times, with 250 milliliter of CHCl3 per wash. Residual CHCl3 was removed in vacuum, the precipitate was redissolved in 500 milliliters of distilled water, and the aqueous solution was refluxed at 100° C. for 18 hours to produce crude geminal diphosphonate polymer product. The aqueous solution containing the crude product was concentrated to about 200 milliliters under vacuum at 50° C., then 1.2 liters of acetone were added. The oily geminal diphosphonate polymer was recovered by decantation.

The precipitation procedure was carried out an additional four times, to produce 72 grams of geminal diphosphonate polymer product. Examination of the product by $P^{31}$ NMR analysis indicated that 43 mole % of the phosphorous in the product was present as hydroxydiphosphonic acid. The product contained 12.28 wt. % total phosphorous. The mole ratio of a/b was calculated to be about 4.0.

EXAMPLE IV

This example shows the synthesis of a geminal polydiphosphonate polymer formed by polymerization of a monomer of the type described by Formula (3). The following steps were performed:

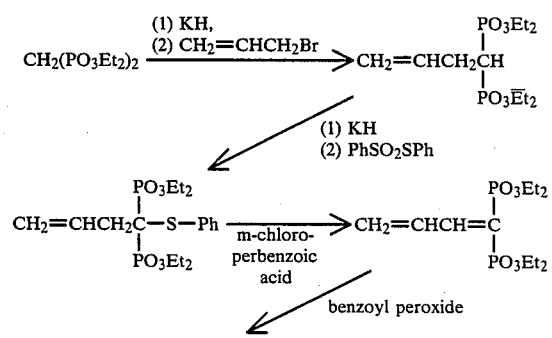

-continued

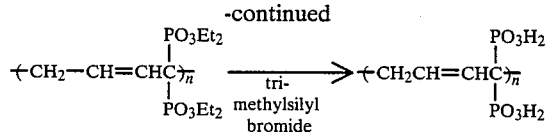

Specifically, to an oven-dried flask under argon was added 11.93 grams of 35% potassium hydride (KH) in mineral oil (0.104 moles). The KH was washed several times with dry toluene to remove the mineral oil. Toluene was added, the mixture was chilled in an ice bath and 30.00 grams of freshly-distilled tetraethyl·methylenediphosphonate (0.104 moles) in 100 milliliters toluene was added dropwise. The mixture was then stirred for 1 hour at room temperature. This solution was then placed in a drop funnel and was added dropwise over a 2.5 hour period to a stirred solution of allyl bromide (12.58 grams, 0.104 moles) in 250 milliliters toluene at 60° C. The solution was stirred at room temperature for an additional 18 hours. The reaction mixture was whtn stripped of toluene and redissolved in 600 milliliters of ethyl ether. The ether solution was washed with water (three times with 100 milliliters per wash), with brine (two times with 100 milliliters per wash), and dried over anhydrous MgSO$_4$. The solids were filtered and the filtrate concentrated at 30° C. to afford 35.12 grams of product (a clear liquid). The crude product was purified on silica gel with 1:1 hexane:acetone as the eluant to give 9.5 grams of tetraethyl 3-butene-1,1-diphosphonate product, as determined by $^{31}$P NMR analysis.

Next, to a dry flask was added 2.85 grams of 35% potassium hydride (KH) in mineral oil (0.0286 moles KH) and washed clean of the mineral oil with 10 milliliter portions of dry toluene. Toluene (75 milliliters) was then added and the mixture chilled in an ice bath while 9.40 grams of tetraethyl 3-butene-1,1-diphosphonate (0.0286 moles) in 25 milliliters of toluene was added dropwise under argon. The solution was stirred at room temperature for 1 hour and then recooled in an ice bath. A solution of 7.16 grams of S-phenylbenzenethiosulfonate (0.0286 moles) dissolved in 50 milliliters of toluene was added dropwise to the stirred solution. The mixture was stirred for 18 hours at room temperature, concentrated, then redissolved in 250 milliliters ethyl ether. The ether solution was washed with water (three times with 50 milliliters per wash), brine (one time with 50 milliliters), and dried over anhydrous MgSO$_4$. The mixture was filtered and the solution concentrated to give 13 grams crude product. The product was purified by chromatography on silica gel with 2:1 hexane-acetone as the eluant to afford 9.85 grams of tetraethyl 1-phenylthio-3-butene-1,1-diphosphonate product, as determined by $^{31}$P NMR analysis.

In a 250 milliliter flask was placed 3.00 grams of tetraethyl 1-phenylthio-3-butene-1,1-diphosphonate (0.00687 moles) in 50 milliliters of (ethanol-free) CHCl$_3$ and stirred at 0° C. under argon. To the stirred solution was added dropwise 1.56 grams of meta-chloroperbenzoic acid in 25 milliliters of CHCl$_3$. Stirring was continued at 0° C. for 1 hour and then for 18 hours at room temperature. The reaction mixture was cooled to 0° C. and 50 milliliters of 10% sodium thiosulfate solution were added. The cold solution was placed in a separatory funnel and the CHCl$_3$ layer isolated. The CHCl$_3$ solution was then washed with saturated sodium bicarbonate solution (2×20 milliliters), water (2×25 milliliters), and dried over anhydrous MgSO$_4$. After filtering, the solution was concentrated to give 3.0 grams of crude product. The crude product was purified by chromatography on silica gel with 2:1 hexane:acetone as the eluant. The chromatography afforded 1.35 grams (60%) of tetraethyl 1,3-butadiene-1,1-diphosphonate product, as determined by $^{31}$P NMR analysis.

In a 25 milliliter roundbottom flask was placed 1.35 grams of tetraethyl 1,3-butadiene-1,1-diphosphonate (4.14 millimoles) and 15 milliliters of benzene and the solution was degassed to remove oxygen. Benzoyl peroxide (10 milligrams, 0.04 millimoles) was added and the solution heated under argon to 60° C. in an oil bath. The reaction was monitored by $^{31}$P NMR. An additional 10 milligram increments of benzoyl peroxide were added after 26, 50, and 74 hours of reaction time. After 74 hours, the solvent was removed under vacuum at 30° C. to provide 1.37 grams of a solid tetraethyl 1,3-butadiene-1,1-diphosphonate polymer product, as determined by $^{31}$P NMR analysis.

The tetraethyl 1,3-butadiene-1,1-diphosphonate polymer was placed in a 25 milliliter flask with 15 milliliters of CHCl$_3$ and 4.90 grams (0.032 moles) of trimethylsilyl bromide. The mixture was stirred at 60° C. for 18 hours, then concentrated at room temperature under vacuum. The product was stirred in 10 milliliters of methanol for several minutes, then the solution was concentrated. This was repeated three times to afford 1.15 grams of crude 1,3-butadiene-1,1-diphosphonate polymer as determined by P$^{31}$ NMR analysis. This polymer was further purified by chromatography on a column of Sephadex G-25 (MW cutoff 5,000) packing.

EXAMPLE V

The following is a representative example of a toothpaste of the present invention.

| Component | % |
| --- | --- |
| Distilled Water | 16.50 |
| Sorbitol (70% Aqueous Solution) | 49.56 |
| Sodium Saccharin | 0.30 |
| Dye Solution | 0.35 |
| Precipitated Silica | 20.00 |
| Sodium Fluoride | 0.25 |
| Flavor | 1.30 |
| Sodium Alkyl Sulfate (27.9% Aqueous Solution) | 5.00 |
| Carbopol 940s* | 0.20 |
| Xanthan Gum | 0.60 |
| Geminal Diphosphonate Polymer of Example I | 6.00 |
| | 100.00 |

The above composition is made by combining the water and part of the sorbitol in an agitated mixture and heating this mixture to 140° F. The geminal diphosphonate polymer, saccharin, sodium fluoride and precipitated silica are then added in order and the total mixture is mixed for from 5 to 10 minutes. The flavor, dye and surfactant are then added. In a separate vessel the remainder of the sorbitol, the Carbopol and the xanthan gum are slurried together and then added to the main mix tank. The complete batch is mixed for about one-half hour and subsequently milled and deaerated.

Alternately, the geminal diphosphonate polymer can be prepared as described in Examples II, III, or IV.

EXAMPLE VI

The following is another representative toothpaste of the present invention.

| Component | % |
| --- | --- |
| Sorbitol (70% Aqueous Solution) | 50.75 |
| Distilled Water | 16.50 |
| Sodium Saccharin | 0.30 |
| Dye Solution | 0.35 |
| Precipitated Silica | 20.00 |
| Sodium Fluoride | 0.25 |
| Flavor | 1.30 |
| Sodium Alkyl Sulfate (27.9% Aqueous Solution) | 5.00 |
| Carbopol 940S | 0.20 |
| Xanthan Gum | 0.60 |
| Geminal Diphosphonate Polymer of Example I | 4.15 |
| | 100.00 |

Alternately, the geminal diphosphonate polymer can be prepared as described in Examples II, III, or IV.

In addition to the levels and combinations of ingredients shown in these examples, others can be used which are consistent with the invention disclosed.

EXAMPLE VII

This example shows a mouth rinse composition containing a geminal diphosphonate polymer of the present invention.

The mouth rinse is prepared as follows:

| Component | % |
| --- | --- |
| Geminal Diphosphonate Polymer of Example I | 4.00 |
| Distilled H$_2$O | 69.19 |
| Ethanol | 16.25 |
| Glycerin | 10.00 |
| Nonionic Surfactant | 0.12 |
| Benzoic Acid | 0.05 |
| Na Saccharin | 0.05 |
| Flavor | 0.15 |
| Color | 0.04 |
| NaOH (10% Sol.) | 0.15 |
| | 100.00 |

The mouth rinse is prepared by adding each of the ingredients to the distilled water and stirring. Alternately the geminal diphosphonate polymer can be prepared as described in Examples II, III, or IV.

What is claimed is:

1. An oral care composition formulated for administration to the oral cavity without substantial ingestion, said composition comprising:

(a) a geminal diphosphonate polymer component wherein said component contains one or more geminal diphosphonate polymers selected from the group consisting of polymers containing the following monomeric unit combinations:

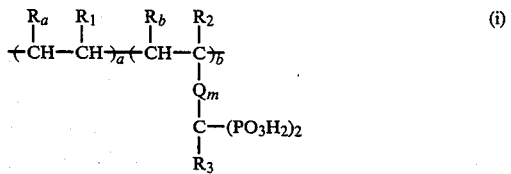

wherein each $R_1$, $R_2$, $R_a$, and $R_b$ can independently be —H, —CO$_2$H or ester thereof, —PO$_3$H$_2$, —C≡N, substituted or unsubstituted aryl, substituted or unsubstituted C$_1$–C$_{10}$ alkyl, or substituted or unsubstituted C$_1$–C$_{20}$ oxyalkyl, each $R_3$ can independently be —H, —OH, amine, or substituted or unsubstituted C$_1$–C$_3$ alkyl, each m can independently be 0 or 1, each Q can independently be a substituted or unsubstituted aryl or a substituted or unsubstituted C$_1$–C$_{10}$ alkylene, and the molar ratio of a/b is greater than or equal to 0 and less than about 30;

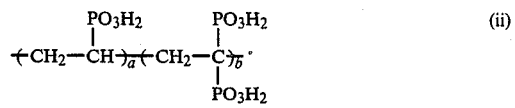

wherein the molar ratio of a/b is greater than or equal to 0 and less than about 30; and (iii) polymerization products of

wherein each X can independently be —H or a C$_1$–C$_{10}$ alkyl, and when X is an alkyl, each —PO$_3$X$_2$ group is converted to a —PO$_3$H$_2$ group subsequent to polymerization; said geminal diphosphonate polymer component having an average molecular weight of between about 1,000 and about 20,000, an average of at least three geminal diphosphonate units per polymer chain, and a molar ratio of monomeric units not containing a geminal diphosphonate to monomeric units containing a geminal diphosphonate of less than about 30; and (b) a pharmaceutically acceptable carrier; said composition containing between about 0.1 wt. % and about 20 wt. % of said geminal diphosphonate polymer component.

2. An oral care composition as in claim 1, wherein said composition is a dentrifrice or prophylactic composition.

3. The oral care composition of claim 2, wherein the average molecular weight of said geminal diphosphonate polymer has an average molecular weight of between about 1,000 and about 5,000.

4. The oral care composition of claim 3, wherein said average molecular weight is between about 2,000 and about 5,000.

5. The oral care composition of claim 2, wherein said composition contains between about 1% and about 10%, by weight of the composition, of said geminal diphosphonate polymer component.

6. The oral care composition of claim 4, wherein said composition contains between about 1% and about 5%, by weight of the composition, of said geminal diphosphonate polymer component.

7. The oral care composition of claim 2, wherein the molar ratio of a/b for Formula (i) and (ii) geminal diphosphonate polymers is less than about 20.

8. The oral care composition of claim 3, wherein the molar ratio of a/b for Formula (i) and (ii) geminal diphosphonate polymers is less than about 20.

9. The oral care composition of claim 6, wherein the molar ratio of a/b for Formula (i) and (ii) geminal diphosphonate polymers is less than about 20.

10. The oral care composition of claim 2, wherein said geminal diphosphonate polymer component is selected from the group consisting of the Formula (i) geminal diphosphonate polymers.

11. The oral care composition of claim 7, wherein said geminal diphosphonate polymer component is selected from the group consisting of polymers containing the following monomeric unit combinations:

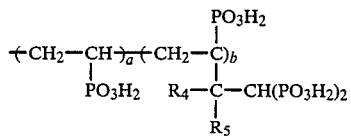

wherein each $R_4$ and $R_5$ can independently be —H, or a substituted or unsubstituted $C_1$-$C_{10}$ alkyl;

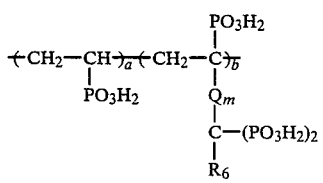

wherein each $R_6$ can independently be —H, substituted or unsubstituted $C_1$-$C_{10}$ alkyl, m is 1, and each Q can independently be substituted or unsubstituted aryl, or substituted or unsubstituted $C_2$-$C_{10}$ alkylene; and

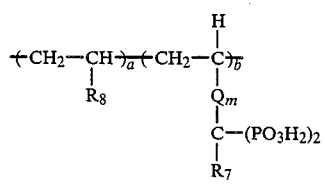

wherein each m can independently be 0 or 1, each Q can independently be substituted or unsubstituted aryl or substituted or unsubstituted $C_1$-$C_{10}$ alkylene, each $R_7$ can independently be —OH, —NH$_2$, or a salt thereof, and each $R_8$ can independently be —CO$_2$H or —C≡N.

12. The oral composition of claim 11, wherein each $R_4$ and $R_5$ of the Formula (i-a) polymers independently is —H or an unsubstituted $C_1$-$C_3$ alkyl, each $R_6$ of the Formula (i-b) polymers independently is —H or an unsubstituted $C_1$-$C_3$ alkyl, and for the Formula (i-c) polymers, each $R_7$ is —OH or a salt thereof, each $R_8$ is —CO$_2$H, and m is 0 or each Q independently is a $C_1$-$C_3$ alkylene.

13. The oral care composition of claim 12, wherein said geminal diphosphonate polymer component is selected from the group consisting of the Formula (i-c) geminal diphosphonate polymers.

14. The oral care composition of claim 13, wherein the average molecular weight of said Formula (i-c) geminal diphosphonate polymer is between about 1,000 and about 5,000.

15. The oral care composition of claim 14, wherein the molecular weight of said Formula (i-c) geminal diphosphonate polymer is between about 2,000 and about 5,000.

16. The oral care composition of claim 15, wherein m is 0, or when m is 0 or Q is an unsubstituted $C_1$-$C_3$ alkylene, and the ratio of a/b is between about 0.5 and about 20.

17. The oral care composition of claim 13, wherein said composition comprises between about 1% and about 10% of said geminal diphosphonate polymer component.

18. The oral care composition of claim 16, wherein said composition comprises between about 1% and about 10% of said geminal diphosphonate polymer component.

19. The oral composition of claim 2 formulated as a dentifrice paste, powder, or gel.

20. The oral composition of claim 11 formulated as a dentifrice paste, powder, or gel.

21. The oral composition of claim 18 formulated as a dentifrice paste, powder, or gel.

22. The oral composition of claim 2 formulated as a mouth rinse composition.

23. The oral composition of claim 11 formulated as a mouth rinse composition.

24. The oral composition of claim 18 formulated as a mouth rinse composition.

25. A method of inhibiting the formation of calculus, said method comprising the step of administering to the oral cavity a pharmaceutically safe and effective amount of one or more geminal diphosphonate polymers selected from the group consisting of polymers containing the following monomeric unit combinations:

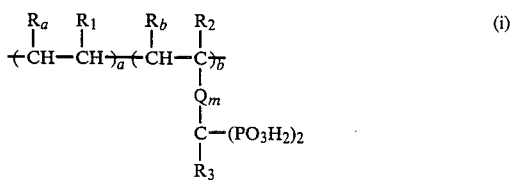

wherein each $R_1$, $R_2$, $R_a$, and $R_b$ can independently be —H, —CO$_2$H or ester thereof, —PO$_3$H$_2$, —C≡N, substituted or unsubstituted aryl, or substituted or unsubstituted $C_1$-$C_{10}$ alkyl, substituted or unsubstituted $C_1$-$C_{20}$ oxyalkyl, each $R_3$ can independently be —H, —OH, or substituted or unsubstituted $C_1$-$C_3$ alkyl, each m can independently be 0 or 1, each Q can independently be a substituted or unsubstituted aryl or a substituted or unsubstituted $C_1$-$C_{10}$ alkylene, and the molar ratio of a/b is greater than or equal to 0 and less than about 30;

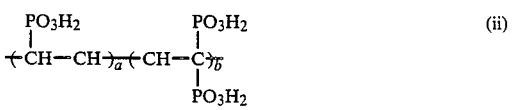

wherein the molar ratio of a/b is greater than or equal to 0 and less than about 30; and (iii) polymerization products of $$CH_2=CH-CH=C(PO_3X_2)_2$$

wherein each X can independently be —H or a $C_1$-$C_{10}$ alkyl, and when X is an alkyl, each —PO$_3$X$_2$ group is converted to a —PO$_3$H$_2$ group subsequent to polymerizations;

said geminal diphosphonate polymer component having an average molecular weight of between about 1,000 and about 20,000, an average of at least three geminal diphosphonate units per polymer chain, and a molar ratio of monomeric units not containing a geminal diphosphonate to monomeric units containing a geminal diphosphonate of less than about 30.

26. A method of inhibiting the formation of calculus as in claim 25, wherein said geminal diphosphonate polymer is selected from the group consisting of polymers containing the following monomeric unit combinations:

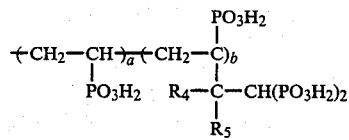
(i-a)

wherein each $R_4$ and $R_5$ can independently be —H, or a substituted or unsubstituted $C_1$-$C_{10}$ alkyl;

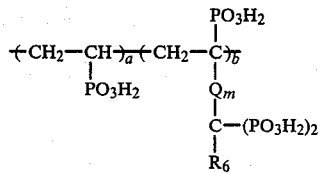
(i-b)

wherein each $R_6$ can independently be —H, substituted or unsubstituted $C_1$-$C_{10}$ alkyl, m is 1, and each Q can independently be substituted or unsubstituted aryl, or substituted or unsubstituted $C_2$-$C_{10}$ alkylene; and

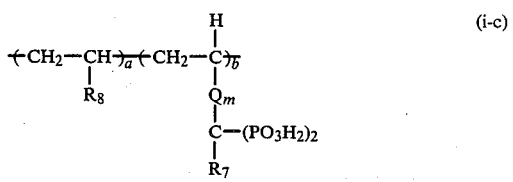
(i-c)

wherein each m can independently be 0 or 1, each Q can independently be substituted or unsubstituted aryl or substituted or unsubstituted $C_1$-$C_{10}$ alkylene, each $R_7$ can independently be —OH, —$NH_2$, or a salt thereof, and each $R_8$ can independently be —$CO_2H$ or —C≡N, and wherein the ratio of a/b is less than about 20.

27. A method of inhibiting the formation of calculus as in claim 26, wherein said method also is effective for inhibiting plaque.

* * * * *